US00PP14228P29

(12) United States Plant Patent
Woolmore

(10) Patent No.: US PP14,228 P2
(45) Date of Patent: Oct. 14, 2003

(54) PHORMIUM PLANT NAMED 'MERLOT'

(50) Latin Name: *Phormium tenax*
Varietal Denomination: Merlot

(75) Inventor: Malcolm Woolmore, Auckland (NZ)

(73) Assignee: Lyndale Nureries, Auckland (NZ)

( * ) Notice: Subject to any disclaimer, the term of this patent is extended or adjusted under 35 U.S.C. 154(b) by 0 days.

(21) Appl. No.: 10/210,622

(22) Filed: Jul. 31, 2002

(51) Int. Cl.[7] ..... A01H 5/00
(52) U.S. Cl. ..... Plt./373
(58) Field of Search ..... Plt./373

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Phormium plant named 'Merlot', characterized by its upright plant habit; stiff, leathery, tough and durable foliage; dark grayed purple upper leaf surfaces with distinct black leaf margin and midrib; and silvery gray lower leaf surfaces.

2 Drawing Sheets

Botanical classification/cultivar designation: *Phormium tenax* cultivar Merlot.

BACKGROUND OF THE INVENTION

The present Invention relates to a new and distinct cultivar of Phormium plant, botanically known as *Phormium tenax,* and hereinafter referred to by the name 'Merlot'.

The new Phormium is a naturally-occurring whole plant mutation of the *Phormium tenax* cultivar Burgundy, not patented. The new Phormium was discovered and selected by the Inventor as a plant within a population of plants of the parent cultivar in a controlled environment in Auckland, New Zealand in 1999.

Asexual reproduction of the new cultivar by divisions taken at Auckland, New Zealand since November, 1999, has shown that the unique features of this new Phormium are stable and reproduced true to type in successive generations.

SUMMARY OF THE INVENTION

The following traits have been repeatedly observed and are determined to be the unique characteristics of 'Merlot'. These characteristics in combination distinguish 'Merlot' as a new and distinct Phormium cultivar:

1. Upright plant habit.
2. Stiff, leathery, tough and durable foliage.
3. Upper leaf surfaces, dark grayed purple in color with distinct black leaf margin and midrib; lower leaf surfaces, silvery gray in color.

Plants of the new Phormium differ from plants of the parent, the cultivar Burgundy, in the following characteristics:

1. Plants of the new Phormium have narrower leaves than plants of the cultivar Burgundy.
2. Leaves of plants of the new Phormium are slightly folded upright whereas leaves of plants of the cultivar Burgundy are flat.
3. Leaves of plants of the new Phormium are darker in color than leaves of plants of the cultivar Burgundy.

Plants of the new Phormium can be compared to plants of the Phormium cultivar Platts Black, not patented. In side-by-side comparisons conducted in Auckland, New Zealand, plants of the new Phormium differed from plants of the cultivar Platts Black in the following characteristics:

1. Plants of the new Phormium were larger, more upright and not as outwardly weeping as plants of the cultivar Platts Black.
2. Plants of the new Phormium had broader leaves than plants of the cultivar Platts Black.
3. Leaves of plants of the new Phormium were slightly folded upright whereas leaves of plants of the cultivar Platts Black were flat.
4. Upper leaf surfaces of plants of the new Phormium were dark grayed purple in color whereas upper leaf surfaces of plants of the cultivar Platts Black were grayish black in color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Phormium. The photograph on the first sheet comprises a side perspective view of a typical plant of 'Merlot' grown in a container. The photograph on the second sheet comprises a close-up view of the upper surface of a typical leaf of 'Merlot'.

DETAILED BOTANICAL DESCRIPTION

The cultivar Merlot has not been observed under all possible environmental conditions. The phenotype may vary somewhat with variations in environment such as temperature and light intensity, without, however, any variance in genotype. The aforementioned photographs and the following observations and measurements describe plants grown in Auckland, New Zealand under commercial practice in an outdoor nursery with day temperatures ranging from 18 to 28° C. and night temperatures ranging from 9 to 18° C. Plants used in the photographs and following description were about one year old from planting. In the following description, color references are made to The Royal Horticultural Society Colour Chart, 1995 Edition, except where general terms of ordinary dictionary significance are used.

Botanical classification: *Phormium tenax* cultivar Merlot.

Parentage: Naturally-occurring whole plant mutation of *Phormium tenax* cultivar Burgundy, not patented.

Propagation:

*Type.*—By divisions.

*Time to initiate roots.*—About 21 to 28 days at 22° C.

*Time to produce a rooted cutting or liner.*—About 186 to 252 days at 22° C.

*Root description.*—Fleshy and thick; grayed orange in color, close to 163A; freely branching.

Plant description:

*General appearance.*—Basal rosette of leaves. Upright and slightly arching plant form. Vigorous; appropriate for 1.5 to 2-liter containers.

*Plant height.*—About 1.8 meters.

*Plant diameter.*—About 1 meter.

*Foliage description.*—Arrangement: Basal, equitant; simple. Length: Average, about 65 cm. Width: Average, about 6 cm. Thickness: About 0.5 mm at thickest point. Shape: Linear, sword-shaped. Apex: Sharply acute. Base: Acuminate. Margin: Entire. Texture, upper and lower surfaces: Smooth, glabrous; tough, leathery and durable. Lower surface covered with a glaucous pruinose film, Orientation: Stiffly erect; rigid. Aspect: Slightly folded upright. Venation pattern: Parallel. Color: Young leaves, upper surface: 187A; margins, 202A. Young leaves, lower surface: 187A overlaid with 198D. Fully expanded leaves, upper surface: 166A overlaid with 183A; margins, 202A. Fully expanded leaves, lower surface: 166A overlaid with 198D. Midrib: Upper surface: 202A. Lower surface: Same as lamina. Lateral veins: Upper surface: 198D. Lower surface: 187A. Petiole: Length: About 10 cm. Diameter: About 3 cm. Color: 187B.

Flower description: Flower development has not been observed on plants of the new Phormium.

Disease/pest resistance: Plants of the new Phormium have not been observed to be resistant to pathogens and pests common to Phormium.

Temperature tolerance: Plants of the new Phormium have been observed to tolerate temperatures from −5 to 35° C.

It is claimed:

1. A new and distinct cultivar of Phormium plant named 'Merlot', as illustrated and described.

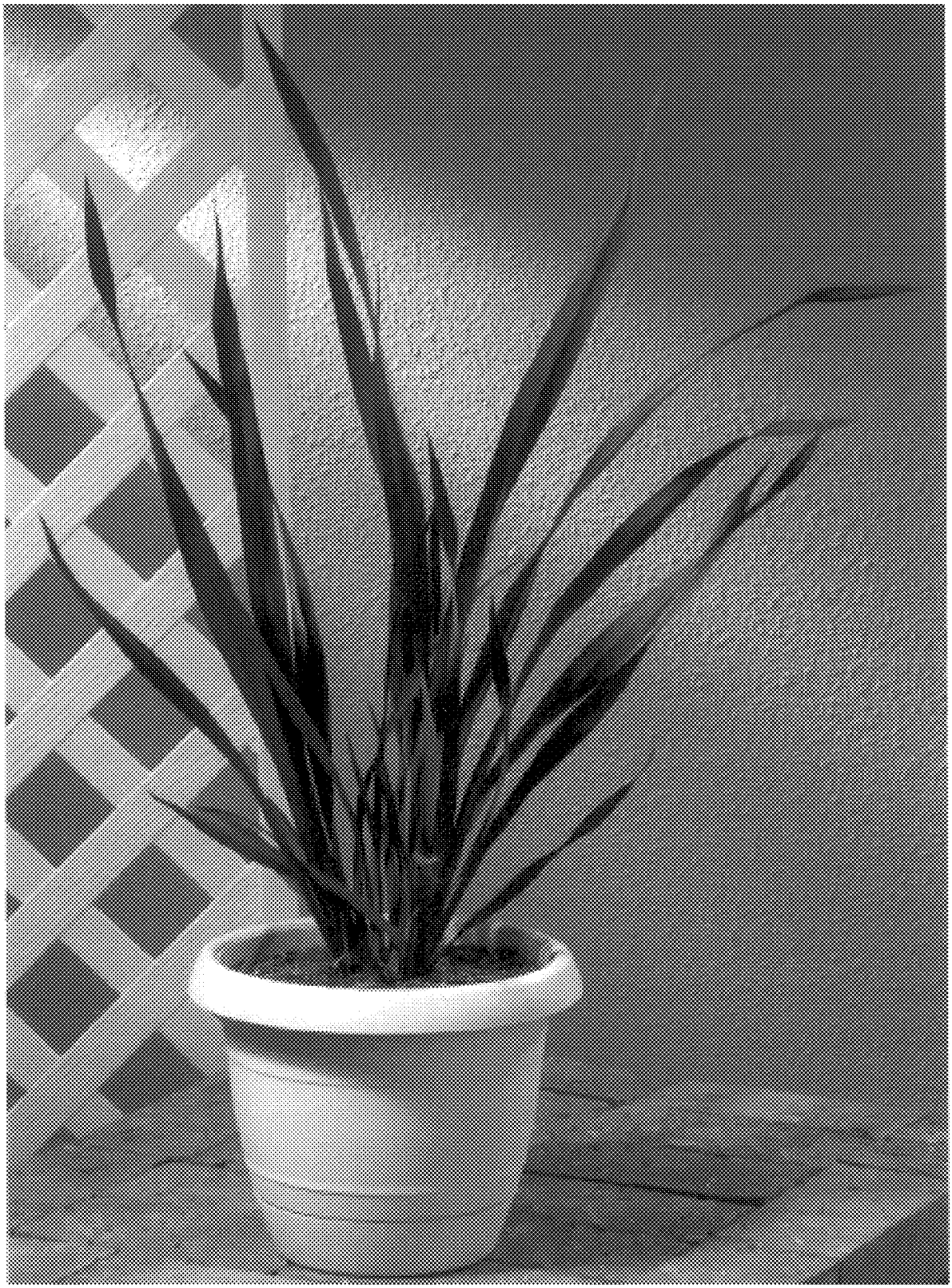

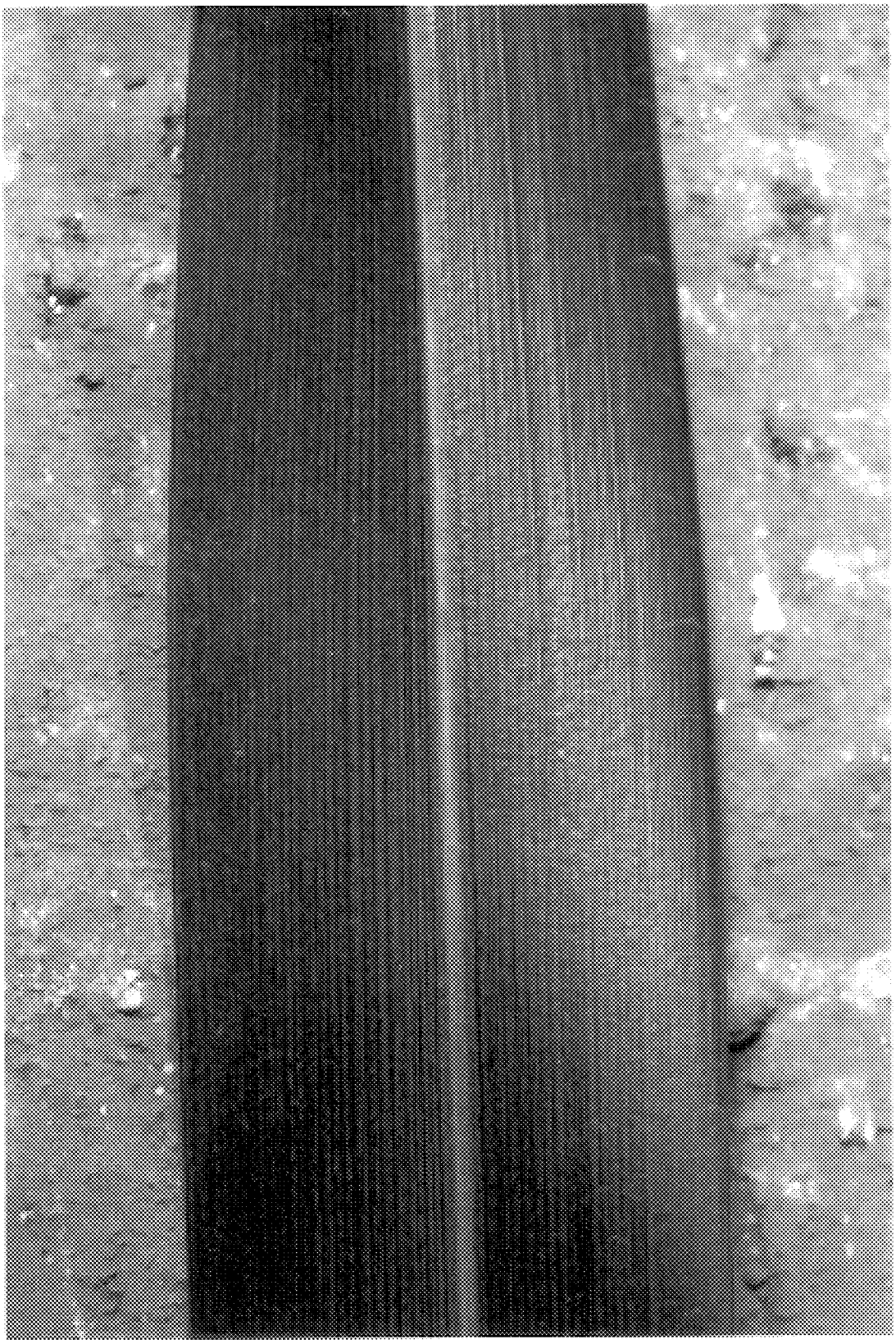

* * * * *